United States Patent [19]

Stevens et al.

[11] Patent Number: 4,857,046
[45] Date of Patent: Aug. 15, 1989

[54] DRIVE CATHETER HAVING HELICAL PUMP DRIVE SHAFT

[75] Inventors: Robert C. Stevens, Williston; Robert R. Braun, Hialeah, both of Fla.

[73] Assignee: Cordis Corporation, Miami, Fla.

[21] Appl. No.: 111,036

[22] Filed: Oct. 21, 1987

[51] Int. Cl.$^4$ .............. A61F 17/20; A61F 17/32
[52] U.S. Cl. ................................ 604/22; 128/305
[58] Field of Search ............. 604/95, 22; 128/305

[56] References Cited

U.S. PATENT DOCUMENTS

| | | |
|---|---|---|
| 3,614,953 | 1/1969 | Moss . |
| 3,732,858 | 5/1973 | Banko . |
| 3,937,222 | 2/1976 | Banko ............................ 128/305 |
| 4,061,146 | 12/1977 | Baehr et al. .................... 128/305 |
| 4,167,944 | 9/1979 | Banko ............................ 128/305 |
| 4,273,128 | 6/1981 | Lary ............................... 128/305 |
| 4,445,509 | 5/1984 | Auth . |
| 4,512,344 | 4/1985 | Barber ............................ 128/305 |
| 4,589,412 | 5/1986 | Kensey . |
| 4,631,052 | 12/1986 | Kensey ............................ 128/305 |
| 4,632,110 | 12/1986 | Sanagi ............................ 128/305 |
| 4,649,919 | 3/1987 | Thimsen et al. ............... 128/305 |
| 4,653,496 | 3/1987 | Bundy et al. .................. 128/305 |
| 4,679,557 | 7/1987 | Opie et al. . |
| 4,728,319 | 3/1988 | Masch ............................ 604/22 |
| 4,732,154 | 3/1988 | Shiber ............................ 128/305 |

FOREIGN PATENT DOCUMENTS 778067 9/1974 U.S.S.R. .

OTHER PUBLICATIONS

Pedalty, Augioplasty Catheters: Opening New Paths, Medtronic Pulse, vol. 5, No. 2, 1987-p. 8, pp. 11-12.

*Primary Examiner*—C. Fred Rosenbaum
*Assistant Examiner*—Kathleen A. Daley
*Attorney, Agent, or Firm*—Watts, Hoffmann, Fisher & Heinke

[57] ABSTRACT

A flexible drive catheter for removing deposits from the inner walls of a blood vessel to increase blood flow through the vessel. The catheter includes an outer sheath and a rotatable core coupled to a distal tip which directly contacts the deposits. An outer surface of the rotatable core defines a screw pump for moving dislodged deposits away from the blood vessel through the catheter sheath to a bifurcating adapter located outside the patient. One opening in the adapter accommodates the rotatable core and a second opening provides a method of monitoring blood pressure in the blood vessel, removing dislodged deposits from the catheter and injecting flushing liquids or clotting control agents into the blood vessel.

8 Claims, 3 Drawing Sheets

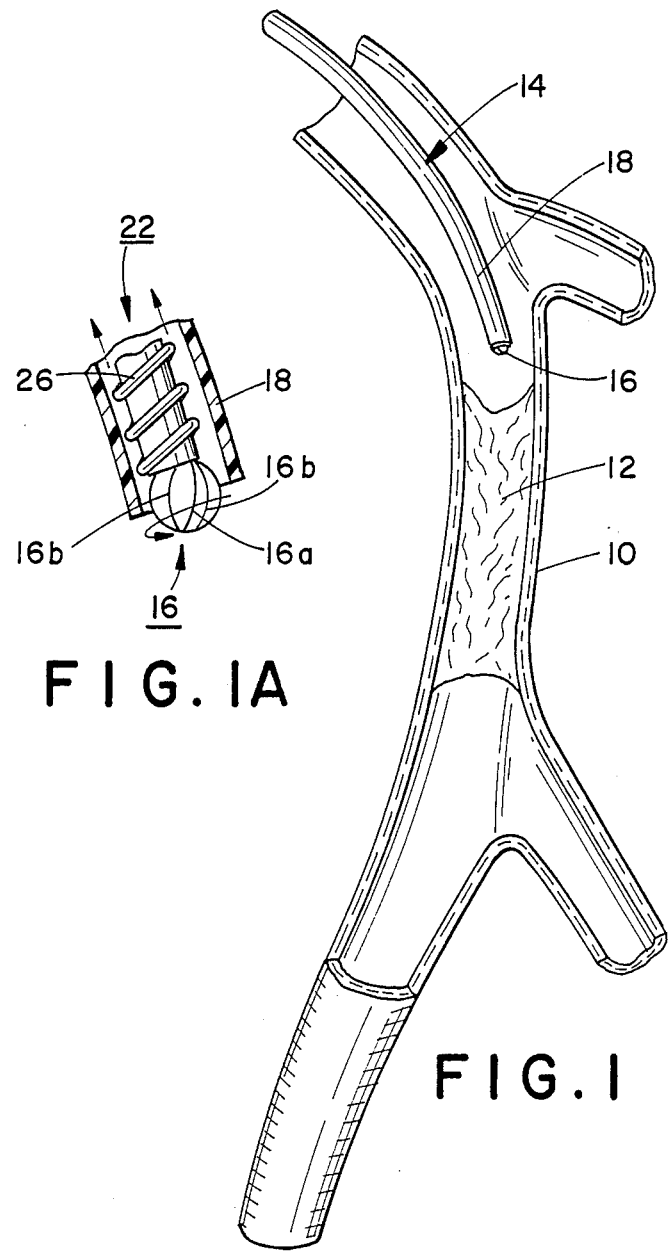

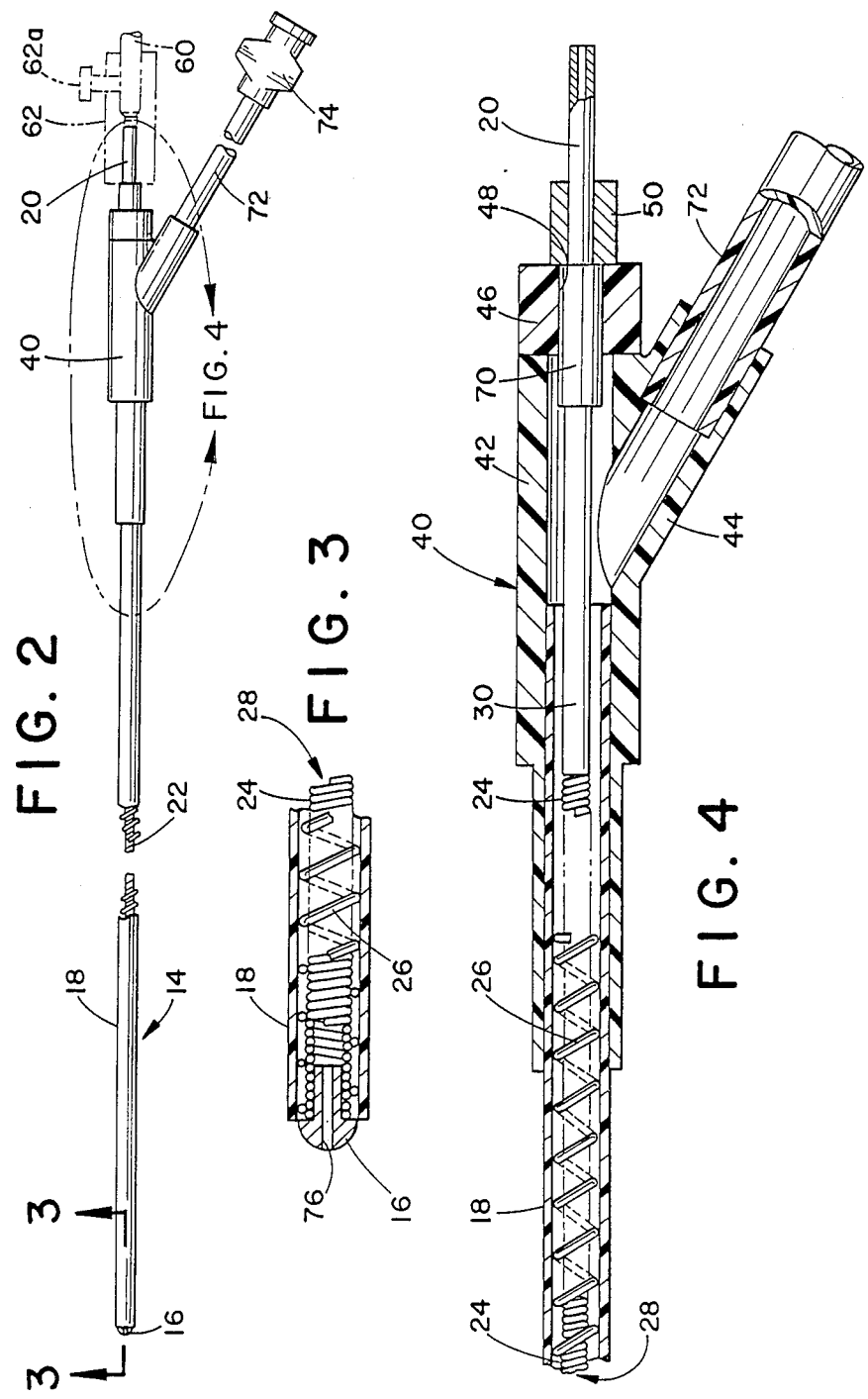

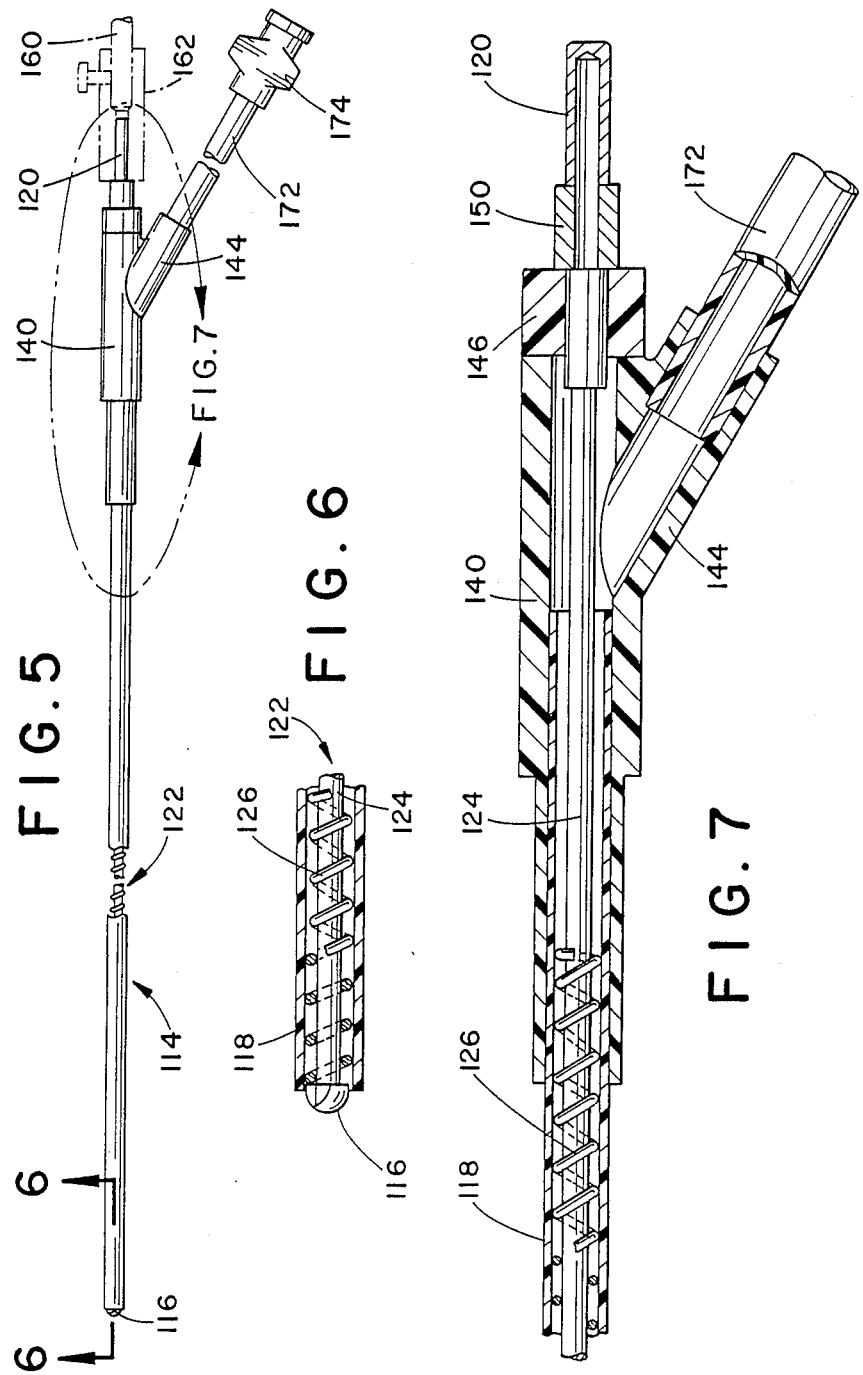

DRIVE CATHETER HAVING HELICAL PUMP DRIVE SHAFT

TECHNICAL FIELD

The present invention relates to a catheter system for opening a totally or partially occluded blood vessel.

BACKGROUND ART

Arteriosclerosis is a condition where deposits build up along an inner surface of a blood vessel and cause a partial or, in extreme cases, a total blockage of the blood vessel. The increase in the number of coronary by-pass operations is some indication of the incidence with which the problem is encountered in older patients.

Prior art proposals recognize that one alternative to bypassing a partially or totally blocked region in a blood vessel is to open or widen the blocked blood vessel. One prior art technique for reopening a blocked blood vessel is to insert a balloon catheter inside the vessel to expand the vessel and either break loose deposits within the vessel or alternatively, increase the size of the lumen passing through those deposits.

An alternate proposal for opening a blocked blood vessel is to bring a high-speed rotating device into contact with occluded portions of the blood vessel. The rotating device produces cutting, abrading, or fluid turbulence to open the vessel and increase blood flow. One device intended for physically opening the blood vessel in this manner is disclosed in U.S. Pat. No. 3,614,953 to Moss entitled "Improvements In or Relating To Drills for Clearing Obstructions". In this patent, a high-speed motor rotates a flexible drive shaft connected to a cutting bit. The bit and flexible drive shaft are inserted into an occluded blood vessel so that when the bit is rotated at high speed and moved into contact with occluded regions it breaks loose deposits within the blood vessel.

A more recent prior art patent disclosing a similar system for opening a blocked blood vessel is disclosed in U.S. Pat. No. 4,445,509 to Auth entitled "Method and Apparatus for Removal of Enclosed Abnormal Deposits". This patent describes a differential cutting tool mounted at a distal end of a flexible shaft which can be inserted into an occluded blood vessel. Again, high speed rotation of the cutting tool causes the tool to remove abnormal deposits from inside the blood vessel.

U.S. Pat. No. 4,589,412 to Kensey entitled "Method and Apparatus for Surgically Removing Remote Deposits" discloses a procedure for removing atherosclerotic plaque. A cutting tip is rotated by the application of fluid pressure through a multi-lumen catheter.

U.S. Pat. No. 4,679,557 to Opie et al. entitled "Electrodynamic Transluminal Angioplasty System" discloses an advancer assembly that includes an off-axis drive that rotates a cutting tool such as that disclosed in the '509 patent to Auth.

The '509 patent to Auth stresses the importance in removing particles separated from an inner wall of the blood vessel. A hollow drive shaft is proposed by Auth to allow suction to be applied to a distal tip of the differential cutting tool disclosed in the '509 patent. It is suggested that particle-entrained blood will flow through the cutting tool to the hollow drive shaft when suction is applied.

USSR Pat. No. 778,067 to Yukhin discloses a helical cutter driven by a flexible shaft for separating blood clots from an internal blood vessel wall. A sheath surrounds the flexible shaft and is connected at a proximal location to a vacuum system for withdrawing separated clot particles from the blood vessel.

U.S. Pat. No. 3,732,858 to Banko discloses a system for removing blood clots, cataracts, and other objects from the eye. At FIG. 12 of this patent a cutting tip is driven by a solid, inflexible shaft having a "helical defining groove . . . such that it acts as a pumping means for removal of the material" (col. 15, lines 44–45) The use of an inflexible shaft makes the Banko system unsuitable for insertion into and passage through a patient's cardiovascular system.

DISCLOSURE OF THE INVENTION

One object of the present invention is a drive catheter having a mechanism for withdrawing dislodged particles and material from an interior region of a blood vessel. A drive catheter constructed in accordance with the invention includes a flexible center drive shaft or core having a length sufficient to extend from outside a subject through the patient's cardiovascular system to an obstructed region within a clogged blood vessel. The flexible core defines a spiraling or helical outer pumping surface to move deposits, plaque and the like separated from the blood vessel inner wall. The core or drive shaft is positioned within a flexible catheter like sheath covering the outer pumping surface of the core.

In one embodiment of the invention the core includes a distal tip portion that is brought into direct contact with the plaque within the blood vessel and which is rotated at high speed by a motor coupled to the core outside the patient. As the catheter core rotates the pumping surface attracts dislodged particles and draw those particles into a region between the catheter sheath and the rotating catheter core. At a proximal end of the catheter, a bifurcating adaptor is connected to the sheath and defines two openings in communication with the interior of the sheath. One adapter opening allows plaque and other deposits to be pumped away from the region between the catheter core and the sheath. The rotatable catheter core extends through the second adapter opening to allow the core to be coupled to a drive motor.

In accordance with one embodiment of the invention, the catheter core comprises an elongated center wire having a second wire wrapped in helical fashion about the center wire from a distal to a proximal portion of the core. This solid core embodiment includes a region at the catheter proximal end not having the outer helically wrapped wire. A smooth outer surface of the center wire can be pushed back and forth through a seal in the catheter's bifurcating adapter to move a distal tip portion of the core back and forth beneath the catheter sheath at the catheter's distal end. This first embodiment can be of a small diameter and therefore is suitable for use in small vessels such as the coronary artery or other small diameter vessels that have become blocked.

In accordance with the second embodiment of the invention, the core comprises a tightly wound center wire that defines a hollow throughpassage leading from the distal portion of the catheter to the proximal adapter coupling. A second wire is helically wound about the tightly wound center wire to define a pumping surface. At the proximal end, the center wire mates with a short piece of tubing which can be pushed back and forth through a seal in the bifurcating adapter to allow the distal tip portion to be maneuvered within the sheath.

This second embodiment of the invention is well suited for use with larger diameter blood vessels such as peripherals. The tightly wound center wire of this embodiment of the drive catheter is more flexible than a similarly dimensioned solid wire. The center wire is wound in the same sense as the helically wound second wire so that it produces a pumping which adds to the pumping produced as the helically wound second wire rotates.

The hollow portion of the second embodiment of the invention extends completely through the core section of the catheter to allow contrast medium or anti-coagulant to be injected from the proximal input through the hollow center section and out the distal tip portion during physical manipulation of the catheter. In addition, the hollow center section of this embodiment allows the catheter to be positioned using a conventional guidewire known in the prior art. In this embodiment, the guidewire is used to position the distal tip portion of the catheter and is then removed prior to motor energization of the catheter core. Both the guidewire and catheter are flexible enough to be routed through the blood vessels leading to the blocked blood vessel. Depending on the location of the obstruction, this can result in a total catheter core length (including the motor coupling) of from 100 to 200 cm.

From the above it is appreciated that one object of the invention is a drive catheter for opening a blocked portion of a blood vessel having a center core member defining a helical pump for withdrawing dislodged material from inside the patient. This and other objects, advantages and features of the invention will become better understood from the detailed description of a preferred embodiment of the invention which is described in conjunction with the accompanying drawings.

BRIEF DESCRIPTION OF THE DRAWINGS

FIG. 1 is a schematic depiction of a blood vessel and a distal portion of an elongated drive catheter positioned within the blood vessel for opening a blocked portion of the blood vessel;

FIG. 1A is an enlarged perspective view of the distal tip portion of the elongated drive catheter of FIG. 1;

FIG. 2 is an enlarged side elevation view showing one embodiment of the catheter depicted in FIG. 1;

FIG. 3 is a partially sectioned view as seen from the plane defined by the line 3—3 in FIG. 2;

FIG. 4 is an enlarged partially sectioned view of a proximal end of the FIG. 1 catheter;

FIG. 5 is an enlarged side elevation view showing an alternate embodiment of a catheter constructed in accordance with the invention;

FIG. 6 is a partially sectioned view of a distal end of elongated catheter of FIG. 5 as seen from the plane defined by the line 6—6 in FIG. 5; and FIG. 7 is an enlarged partially sectioned view of a proximal end of the FIG. 5 catheter.

BEST MODE FOR CARRYING OUT THE INVENTION

Turning now to the drawings, FIG. 1 depicts a blood vessel 10 having an obstructed region 12 where plaque deposits have built up along an extend region of an inner wall surface of the blood vessel 10. In the situation depicted in FIG. 1, the obstruction 12 has impeded the flow of blood through the vessel 10 to the point where a physician has determined via an angiographic study that invasive procedures utilizing a drive catheter 14 can be effectively utilized to remove at least a portion of the deposits 12 from within the inner wall of the blood vessel 10.

In the FIG. 1 depiction, a distal end portion of the catheter 14 has been routed to the vicinity of the obstructions 12 prior to motor energization of the catheter 14 to effect a rotation of a distal tip 16. Procedures for maneuvering elongated catheters for both balloon angioplasty as well as diagnostic angiography are well known in the prior art. In accordance with one procedure, a catheter guidewire is inserted into the patient and the passage of this guidewire monitored through the patient on an x-ray imaging screen. When the guidewire has been properly positioned within the patient, prior art catheter systems are slipped over the guidewire and inserted along the guidewire path into the blood vessel of interest. During the insertion of the catheter, it is also well known to inject contrast medium which shows up on the x-ray viewing screen to aid the physician in properly positioning the catheter.

FIG. 2 depicts a first embodiment of the catheter 14. In accordance with the construction of this embodiment, the distal tip 16 is connected to a proximally located drive coupling 20 by an elongated flexible catheter core 22 rotatably supported by a generally cylindrical flexible outer sheath 18.

The core 22 comprises a first tightly wound inner wire 24 and a second outer wire 26 helically wound about and attached by soldering or the like to the first wire 24. In combination, the wires 24, 26 define a through-passage 28 extending through the catheter 14 to a proximal end of the catheter. The second wire 26 terminates near the proximal end of the catheter and the inner wire 24 is connected by welding or the like to a hollow metal tube 30 (FIG. 4).

The outer sheath or catheter 18 comprises either a single or multiple layers of extruded plastic either with or without a braided core for stiffening. In a preferred embodiment of the catheter 14, the outer sheath 18 comprises a thin walled catheter having longitudinal stability and constructed of Teflon or the like.

As seen most clearly in FIGS. 2 and 4, at the proximal end of the catheter 14, the outer sheath 18 is connected by heat welding or the like to a plastic bifurcating adapter 40. The adapter 40 defines an inline branch 42 and a side branch 44. The inline branch 42 is defined in part by a separate plastic coupling 46 having a through-passage 48 to accommodate the catheter 14. A stop 50 attached to the drive coupling 20 comprises a cylindrical sleeve physically attached to the coupling 20 by welding or the like and defines an outer diameter greater than the diameter of the opening 48. In the FIG. 4 embodiment the drive coupling 20 is the proximal end of the hollow tube 30. The stop 50 defines a limit of movement through the sheath 18 of the core 22. In particular, this defines a limit for outer movement of the distal tip 16 attached (by welding) to the inner core wire 24 (FIG. 3).

Once the catheter distal tip 16 has been positioned in close proximity to the obstructions 12, a motor having an output shaft 60 is connected to the drive coupling 20 by means of an adapter assembly 62 which includes a threaded connector 62a that engages the motor output shaft 60. Rotational speeds in the range of 5,000 rpm are achieved utilizing a small hand-held direct current motor that is battery powered and specifically adapted for high speed energization of a catheter 14. The high speed rotation of the coupling 20 applies a torque to the core 22 to rotate the distal tip 16 at high speed. The distal tip 16 is then typically brought into contact with the deposits 12 and abrades those deposits to cause them to break loose from the blood vessel.

Both the inner and outer wires 24, 26 rotate in a spiralling manner. Since both wires 24, 26 are wound in the same sense they both produce a pumping action. This pumping action tends to draw dislodged particles of plaque which are separated from an inner wall of the blood vessel 10 into the catheter 14. The core wire 26 acts as a screw pump, not only creating a vortex of fluid within the blood vessel, but also physically carrying deposits along the length of the catheter within the sheath 18 to the vicinity of the side branch 44 of the bifurcated adapter 40. In addition to carrying dislodged particles away from the tip 16, the sheath 18 prevents uncontrolled abrasion of the blood vessel inner wall since the tip 16 cannot extend more than one-half its diameter beyond the distal end of the sheath 18.

As seen more clearly in FIG. 1A, the distal tip 16 has flutes 16a and grooves 16b extending along an outer surface. The flutes 16a spiral in a direction in the same sense as the spiralling helical wire 26 so that deposits an plaque dislodged from the blood vessel wall as the tip 16 contacts the deposits are routed through the grooves 16b to the spiralling core wire 26 and along the region between the more tightly wound inner core wire 24 and the sheath 18.

Experience with the catheter 14 constructed in accordance with the invention indicates that it is desirable to move the distal tip 16 within the sheath 18 and in particular to retract the distal tip 16 from the fully extended position shown in FIG. 3. As noted above, the stop 50 at the proximal end of the catheter 14 prevents movement of the distal tip 16 beyond the position shown in FIG. 3. During the procedure, however, it may be desirable to retract the distal tip 16 a short distance within the catheter sheath 18. To provide this capability, the hollow tubing 28 defines a smooth outer surface which slides back and forth through a plastic seal 70 fixed to the adapter coupling 46. The seal 70 acts as a bearing for the core 22 and allows the tube 28 to slide back and forth a limited distance within the adapter while preventing material pumped along the catheter sheath by the rotating core 22 from exiting the opening 48. Instead, this material, both removed plaque as well as blood that is pumped through the catheter 14, is directed to the side branch 44.

It is also anticipated that the physician may wish to withdraw the core 22 from the sheath 18 without removing the sheath from the patient. With the motor de-energized the core 22 and attached tip can be withdrawn through the seal 70, cleaned and re-inserted into the sheath 18. Also, a different core 22 having a differently configured tip 16 can be used to replace the original.

Coupled to the side branch 44 is a flexible plastic tube 72 having a conventional luer fitting 74 for the attachment of suction applying devices to withdraw the combined plaque and fluids driven along the catheter 14 to the interior of the proximal bifurcating adapter 40. The side branch 44 can also be used to inject a flushing fluid or heparin to control blood clotting. In addition blood pressure monitoring can be performed through this side branch 44.

As seen in FIGS. 2-4, a throughpassage concentric with the core 20 extends completely through the catheter 14. The throughpassage is first defined by a center passageway 76 in the distal tip 16 extends into the center passageway 28 defined by the spiralling inner wire 24 of the core 22 and then through the hollow tube 30. This center passageway accommodates either a guidewire for positioning the catheter 14 or can be utilized for delivering contrast medium out the distal tip 16. When used with a guidewire, the guidewire is positioned within the patient and then a proximal end of the guidewire is slipped over the tip 16 into the catheter 14 and used to guide the catheter to the vicinity of the obstructions 12.

Turning now to FIGS. 5-7, an alternate catheter 114 having a center core 122 and distal tip 116 is depicted. The catheter 114 also includes a motor coupling 120 and mechanical stop 150 for defining the limits of movement for the core 122 within an outer sheath 118. As seen most clearly in FIG. 6, in accordance with this embodiment of the invention, the core 122 includes a solid center flexible wire 124 having a helically spiralling stainless steel wire 126 wrapped about its outer surface. The embodiment of the catheter 114 shown in FIGS. 5-7 therefore does not define a center throughpassageway. Instead, the center wire 124 extends completely through the catheter 114 from the motor coupling 120 to the distal tip 116.

As seen most clearly in FIG. 7, in the vicinity of a bifurcating adapter 140 the outer helically wound wire 126 ends and the center core wire 124 passes through a seal 170 fixed within an inline coupling 146 of the adapter 140. This allows a limited amount of movement back and forth within the catheter sheath 118 of the rotating distal tip 116 and as in the first embodiment of the invention allows the core 122 and tip 116 to be withdrawn from the sheath 118 and then reinserted or replaced.

As in the earlier embodiment of the catheter disclosed in FIGS. 2-4, this alternate embodiment of the catheter 114 is routed to the vicinity of obstructions within a blood vessel. When the distal end of the catheter 114 has been properly positioned within the patient, the motor coupling 120 is energized by a motor having an output shaft 160 fixed to the coupling 120 by an adapter 162. When rotating with the core 122 of speeds up to 5000 rpm the outer helical wire 126 acts as a screw pump to create a vortex at the distal tip of the catheter 114. Dislodged particles of plaque are attracted into the sheath 118 and delivered by the screw pump 126 to the bifurcating adapter 140. As in the earlier embodiment, the side arm 144 opens into a plastic tube 172 having a luer fitting 174 for withdrawing material delivered along the length of the catheter 144 from the obstructed region of the blood vessel.

In both embodiments of the invention, the outer coiled wire is physically bonded at the ends of the core. This is preferably accomplished by welding the outer coiled wire to the core.

The first embodiment of the invention shown in FIGS. 2-4 has dimensions somewhat larger than the second embodiment shown in FIGS. 5-7. In one embodiment, the outside diameter of the helically wound coil 26 is 0.063 inches. The base coil 24 in this embodiment has an outside diameter of 0.038 inches. In the version depicted in FIGS. 5-7, an illustrative embodiment has a solid stainless steel wire for the center member 124 having an outside diameter of 0.014 inches. The outer coiled pump wire 126 is also a stainless steel wire and has an outer diameter of 0.039 inches. In the second embodiment stainless steel wire is used for both helically wrapped outer wire as well as in the inner closely wrapped wire. A preferred outer sheath 18 in the embodiments depicted in FIGS. 2-4 has an outside diameter of 0.087 inches and an inner diameter of 0.073 inches. This leaves a clearance of approximately 3 or 4 thousandths of an inch between the outer coil 26 and an inner wall of the sheath 18. The catheter length depends on how far the catheter must be routed through the cardiovascular system so that lengths up to 200 cm are used.

The present invention has been described with a degree of particularity. The dimensions presented are illustrative and are not intended to limit the scope of the invention. It is the intent, therefore, that the invention include all modifications or alterations falling within the spirit or scope of the appended claims.

We claim:

1. A catheter for removing deposits from the inner walls of an obstructed region of a blood vessel comprising an elongated flexible catheter core of a sufficient length and flexibility to extend from outside a subject through a subject's cardiovascular system to the obstructed region within the blood vessel, said catheter core comprising a center portion having a helical pumping surface that spirals around the center portion along a substantial length of said catheter core for moving deposits separated from the blood vessel inner wall from a distal to a proximal end of said core; said core having an enlarged distal tip for abrading deposits from an inner wall of the blood vessel; an elongated catheter sheath for covering the helical pumping surface of said core; and proximal drive means coupled to the catheter core for rotating the core within the sheath to move deposits removed from the vessel wall out of said blood vessel through a region between said pumping surface of said core and an inner wall of the sheath.

2. The catheter of claim 1 further comprising a proximally located bifurcating adapter coupled to the sheath having first and second openings wherein a first opening communicates with a region beneath the sheath outside the catheter core to receive plaque withdrawn from the vessel and the second opening provides a passageway for routing the core outside the sheath to the drive means.

3. The catheter of claim 2 additionally comprising a seal to inhibit deposits from passing through the second opening along an outer surface of said core and act as a bearing for high speed rotation of said core within the sheath.

4. The catheter of claim 1 wherein the elongated catheter core and proximal drive means define a center passageway through said catheter.

5. The catheter of claim 1 wherein the enlarged a distal tip has flutes that spiral along an outside surface of said tip in the same sense as the spiralling outer pumping surface of the core.

6. The catheter of claim 4 wherein the core comprises an inner wire and outer wire wound around a concentric axis, said inner wire being wound with a relatively tight pitch and the outer wire being wound around the inner wire with a relatively wide pitch.

7. The catheter of claim 6 wherein adjacent coils of the inner wire touch to form a coiled wire cylinder defining at least a portion of said center passageway.

8. The catheter of claim 1 wherein the catheter core comprises a first center wire having a second wire helically wrapped around the center wire.

* * * * *